United States Patent [19]

Summers

[11] 4,372,559

[45] Feb. 8, 1983

[54] EDUCATIONAL GAME FOR STUDENT AND/OR GRADUATE NURSES

[76] Inventor: Ann Summers, 650 Huntington Ave., Boston, Mass. 02115

[21] Appl. No.: 214,226

[22] Filed: Dec. 8, 1980

Related U.S. Application Data

[63] Continuation-in-part of Ser. No. 956,037, Oct. 30, 1978, abandoned.

[51] Int. Cl.³ ............................................. A63F 3/00
[52] U.S. Cl. ................................................... 273/243
[58] Field of Search ...................... 273/242, 243, 249

[56] References Cited

U.S. PATENT DOCUMENTS 4,010,955  3/1977  Nelson ................................. 273/243
4,121,823  10/1978  McBride ........................... 273/243 X
4,136,879  1/1979  Andrew et al. ..................... 273/243

FOREIGN PATENT DOCUMENTS 1482321  8/1977  United Kingdom ................ 273/243

*Primary Examiner*—Richard J. Apley
*Attorney, Agent, or Firm*—Henry C. Nields

[57] ABSTRACT

An educational device employing a game situation to teach student nurses or graduate nurses is disclosed. The educational device is generally comprised of a playing board having a plurality of contiguous areas extending around the perimeter of the board, and also having additional areas in the central region of the board. Most of the contiguous areas are grouped into three groups, designated "acute", "intermediate", and "convalescence". The educational device also includes two decks of cards, one relating to admission onto the playing board, and the other relating to play on the playing board. All of the cards have printed on one side thereof a question relating to the medical field, together with several alternative answers, only one of which is correct. The other side of each card reveals the correct answer, and also has printed thereon instructions as to what to do in the case of a correct answer, and what to do in case of an incorrect answer. The educational device also includes playing pieces for movement on the playing board. The object of the game is to advance around the perimeter of the board, through the groups of contiguous areas in sequence through the "acute", the "intermediate", and the "convalescence" groups. In each turn a player advances by drawing cards from the deck, answering the questions thereon, and following the instructions on the card associated with the answer given.

1 Claim, 4 Drawing Figures

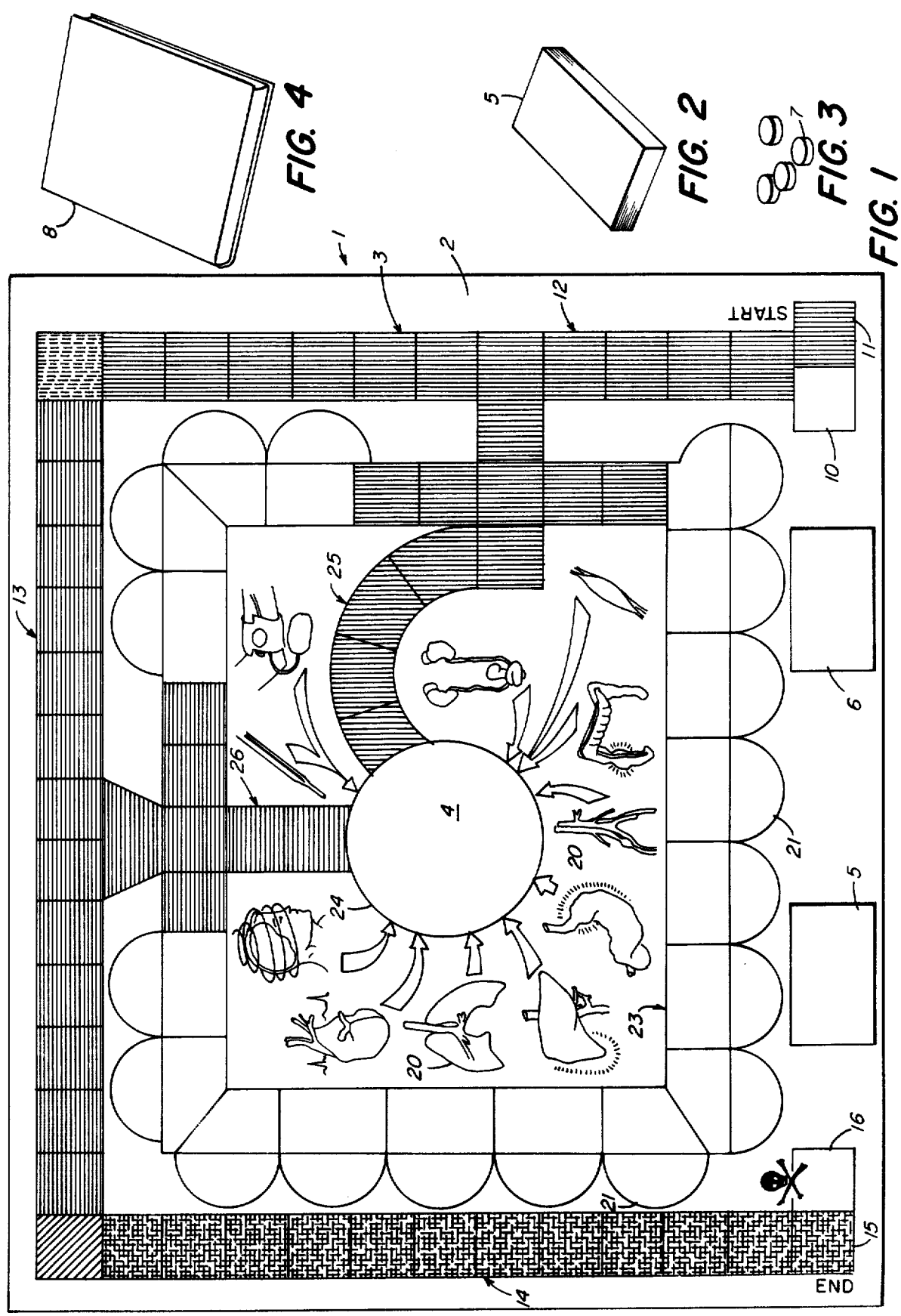

EDUCATIONAL GAME FOR STUDENT AND/OR GRADUATE NURSES

This is a continuation-in-part of application Ser. No. 956,037 filed Oct. 30, 1978 now abandoned.

FIELD OF THE INVENTION

This invention relates to educational devices, and more specifically to educational devices employing game situations to teach student nurses or graduate nurses.

BACKGROUND OF THE INVENTION

Educational devices for teaching various subject matter have been in use for many years. In most cases, such educational devices have employed flash cards, tables, and other similar devices. Educational devices employing a game situation have also been proposed, such as those disclosed in U.S. Pat. No. 4,121,823. The present educational device is of the same general type as that disclosed in said U.S. Pat. No. 4,121,823, and therefore includes many of the advantages set forth in said patent. However, the present invention is especially adapted to teach student nurses or graduate nurses, and therefore differs from the disclosure of said U.S. Pat. No. 4,121,823 in various important respects.

SUMMARY OF THE INVENTION

The present invention provides an educational device employing a game situation to teach student nurses or graduate nurses, and accomplishes the following purposes and educational objectives:

PURPOSES AND EDUCATIONAL OBJECTIVES

1. To intensify the knowledge of students and/or graduate nurses of the signs and symptoms of specific pathophysiological conditions in an application situation.

2. To encourage students and/or graduate nurses to analyze their own actions with a certain detachment relative to the information presented to them in a simulated situation without any formal grading involved.

3. To allow students and/or graduate nurses to choose alternatives in a simulated situation that may be wrong without endangering the welfare of real clients.

4. To increase the awareness in students and/or graduate nurses of how their actions effect the progress of clients.

SCOPE

The game begins with admission of clients to the hospital through the choice of correct alternatives using the admission playing cards.

The game ends when the first and second players successfully move their clients, through the acute, intermediate and convalescent stages of illness back to the community through the correct use of alternatives.

ACTORS

The players are 2 to 4 student or graduate nurses. One extra person may be included or delegated to act as the reference reader if so desired by the group. If not, each player can do her/his own reading. The playing pieces are clients.

ACTORS OBJECTIVES

To choose alternatives at appropriate recovery levels of clients illnesses that will speed the clients recovery and subsequent discharge without incurring penalties or being excluded from the game prematurely.

The educational device is typically comprised of a playing board having a plurality of contiguous areas located around the perimeter thereof, two card decks, a plurality of markers, and a book containing medical information in greater detail than is contained on the cards. Most of the contiguous areas are divided into three groups, designated "acute", "intermediate", and "convalescence".

All of the cards have printed on one side thereof a question relating to the medical field, together with several alternative answers, only one of which is correct. The other side of each card reveals the correct answer, and also has printed thereon instructions as to what to do in the case of a correct answer, and what to do in the case of an incorrect answer.

The object of the game is to travel the entire perimeter of the game board, traveling in sequence through the "acute" group, the "intermediate" group, and the "convalescence" group. Each player has a playing piece, and in order to place this piece on the playing board at the "admission" end of the contiguous areas, each player draws a card from the "admissions" deck, answers the question thereon, and follows the instruction associated with her answer. Thereafter, each player draws only from the "intervention" deck, answers the question thereon and follows the instruction associated with her answer. The answer side of each card in the "intervention" deck also indicates whether the correct intervention may be made at any of the three stages (acute, intermediate or convalescence), or whether the correct intervention may only be made at one or two such stages. The various instructions include, not only movement among the contiguous areas, but also movement onto the central region of the board as a penalty for giving a wrong answer. The object of the game, as noted above, is to travel the perimeter of the board through the contiguous areas, and ultimately to reach the "discharge" end of the contiguous areas.

DESCRIPTION OF THE DRAWINGS

FIG. 1 is a top plan view of a game apparatus in accordance with the present invention.

FIG. 2 illustrates a question-answer card for use with the game apparatus of FIG. 1 in accordance with the present invention.

FIG. 3 illustrates a playing piece for use with the game apparatus of FIG. 1 in accordance with the present invention.

FIG. 4 illustrates reference materials for use with the game apparatus of FIG. 1 in accordance with the present invention.

DETAILED DESCRIPTION OF THE INVENTION

Referring now to FIG. 1, there is shown therein a top plan view of a game apparatus 1 in accordance with the present invention. The game apparatus 1 is generally comprised of a board 2 having around the perimeter thereof a plurality of contiguous areas 3 enclosing a central area 4. The game apparatus 1 further compresses an "admission" card deck 5 and an "intervention" card deck 6, a marker 7 for each player, and reference materials 8. Within the central area 4 are various penalty areas 20, 21 which will be described in more detail hereinafter.

One end of the contiguous areas 3 included an area designated an admitting-office area 10 and an emergency-room area 11. Adjacent to these areas 10, 11 is a row of "acute" areas 12, which may be designated on the playing board 2 by a particular color, such as red (not shown). Adjacent the acute areas 12, and continuing in sequence therefrom, is a row of "intermediate" areas 13, which may be designated on the playing board 2 by another particular color, such as blue (not shown). Adjacent the intermediate areas 13, and continuing in sequence therefrom, is a row of "convalescence" areas 14, which may be designated on the playing board 2 by still another particular color, such as yellow (not shown). Adjacent the convalescence areas 14, and continuing in sequence therefrom, are a discharge area 15 and a morgue 16.

The central area 4 includes various penalty areas 20, 21. Some of these areas represent organs 20 of the body. In certain cases the consequence of an incorrect intervention is to have an adverse effect on a certain organ of the body, and the answer side of the corresponding intervention card will direct the player choosing the wrong alternative to move her playing piece onto the corresponding organ-type penalty area 20 of the board 2. Recovery from the penalty area 20 is accomplished, following directions on the intervention cards, via the "nursing-rounds-medical" area 24, and thence to the stage of the patient's condition at which the playing piece was located at the time the penalty was imposed. For example, if the penalty was imposed while the playing piece was in the acute area 12, then the road to recovery is via the passageway 25 to the acute area 12. If the penalty was imposed while the playing piece was in the intermediate area 13 or the convalescence area 14, the road to recovery is via the passageway 26 to the intermediate area 13.

Other penalty areas 21 represent various hospital departments, such as x-ray, laboratory, blood bank, intravenous therapy, pharmacy, respiratory therapy, operating room, recovery room, cast room, physiotherapy, transplant room, dietary, cashier's office, recreational, speech therapy, social service, psychiatric therapy, occupational therapy, etc. In certain cases the consequence of a wrong alternative may best be illustrated in terms of one of these hospital departments, and the answer side of the corresponding intervention card will direct the player choosing the wrong alternative to move her playing piece onto the corresponding department-type penalty area 21 of the board 2. Recovery from the penalty area 21 is accomplished, following the directions on the intervention cards, via a corridor 23, and thence to the stage of the patient's condition at which the playing piece was located at the time the penalty was imposed, in a manner similar to that employed in recovering from an organ-type penalty area 20.

The board 2 is adaptable to a wide variety of types of questions and answers. Generally an admission card deck 5, an intervention card deck 6, and reference materials 8 constitute a unit dealing with a particular aspect of medical care. Initially a game "package" might be sold with one such unit included, while supplemental units could be purchased separately. Since movement of the playing pieces about the board is governed by the directions on the various cards, a wide variety of playing techniques is possible through the use of various types of directions, etc. The following are illustrative examples of representative admission cards:

Admission Card A1: Question Side

Hattie Green, a 70 year old retired schoolteacher, awoke this morning unable to move side of her body or to speak. She probably:
(a) is righthanded and has suffered a left middle cerebral artery accident (CVA)
(b) is righthanded and has suffered a left anterior cerebral artery accident (CVA)
(c) is righthanded and has suffered a basilar accident (CVA)
(d) is lefthanded and has suffered a right vertebral artery accident (CVA)

Admission Card A1: Answer Side

CORRECT
(a) is righthanded and has suffered a left middle cerebral artery accident (CVA)
INCORRECT
(b) is righthanded and has suffered a left anterior cerebral artery accident (CVA)
(c) is righthanded and has suffered a basilar artery accident (CVA)
(d) is lefthanded and has suffered a right vertebral artery accident
IF CORRECT—CHOOSE PLAYING PIECE AND MOVE ONTO THE BOARD ON SQUARE ONE AFTER EMERGENCY ROOM. IF INCORRECT—TRY AGAIN THE NEXT TURN AROUND Admission Card A2: Question Side Melvin Thomas, 35 years old, married and the father of four children, is brought to the ER unconscious with no history of trauma or injury. He collapsed while playing tennis with his wife. On opthalmic examination, a choked disc was noted on the right and other symptoms of increasing intracranial pressure. It is most likely he has:
(a) blockage of the internal carotid from an atherosclerotic plaque
(b) hemorrhage somewhere in the cerebral circulation due to a ruptured aneurysm
(c) a tumor somewhere near the frontal lobe
(d) a blood clot in the middle cerebral artery Admission Card A2: Answer Side CORRECT
(b) a hemorrhage somewhere in the cerebral circulation due to a ruptured aneurysm
INCORRECT
(a) a blockage of the anterior carotid artery due to an atherosclerotic plaque
(c) a tumor somewhere near the frontal lobe
(d) a blood clot in the middle cerebral artery
IF CORRECT CHOOSE A PLAYING PIECE AND MOVE ONTO THE BOARD ON THE FIRST SQUARE AFTER THE EMERGENCY ROOM. IF NOT CHOOSE ANOTHER CARD THE NEXT TIME AROUND AND TRY AGAIN.

Admission Card A3: Question Side

Thomas Fuller, 56, a black machinist, noticed at work that several times over the last month he has had headaches, dizziness and occasional tendency to drop things that he picks up with his left hand. The symptoms he exhibits are characteristic of which of the following:
(a) a right temporal lobe tumor (b) a left vertebral CVA
(c) hypertension and TIA
(d) a right intracerebral hemorrhage Admission Card A3: Answer Side CORRECT
(c) hypertension and TIA
INCORRECT
(a) right temporal lobe tumor
(b) a left vertebral CVA
(d) a right intracerebral hemorrhage
CORRECT—CHOOSE A PLAYING PIECE AND MOVE ONTO THE BOARD ON SQUARE ONE AFTER EMERGENCY ROOM. INCORRECT—TRY AGAIN THE NEXT TURN AROUND Admission Card A4: Question Side Emily Bromley has suffered several transient ischemic attacks in the past but had a severe attack today. She has been brought to the emergency room with headache, dizziness, flushed face, mental confusion, partial loss of vision and difficulty in swallowing: Two immediate nursing priorites in the ER are:
(a) check blood pressure/give oxygen
(b) loosen clothing around neck and turn client on the side with the bed slightly elevated
(c) check pule and monitor for convulsions
(d) check pupils frequently and leave client flat and turned to the side Admission Card A4: Answer Side CORRECT
(b) loosen clothing around neck and turn client on the side with the head elevated slightly
INCORRECT
(a) check blood pressure/give oxygen
(c) check pulse and monitor for convulsions
(d) check pupils frequently and leave client flat and turned on the side
IF CORRECT—CHOOSE PLAYING PIECE AND MOVE INTO THE BOARD ON SQUARE ONE AFTER EMERGENCY ROOM INCORRECT—TRY AGAIN THE NEXT TURN AROUND Admission Card A5: Question Side George Summers is a 70 year old retired postman. He has been brought to the hospital unconscious. His wife could not awaken him this morning. He is diagnosed after initial examination as a CVA. It is most likely within his age group, that he has suffered:
(a) intracerebral hemorrhage
(b) atherosclerotic plaque obstruction
(c) cerebral thrombosis
(d) trauma from blow on head Admission Card A5: Answer Side CORRECT
(c) cerebral thrombosis
INCORRECT
(a) intracerebral hemorrhage
(b) atherosclerotic plaque obstruction
(d) trauma from blow on the head
CORRECT—CHOOSE A PLAYING PIECE AND MOVE ONTO THE BOARD ON SQUARE ONE AFTER EMERGENCY ROOM. INCORRECT—TRY AGAIN THE NEXT TURN AROUND Admission Card A6: Question Side In clients that have suffered a CVA from a cerebral thrombus, evidence indicates that the most common site for an obstruction to occur is:
(a) basilar artery
(b) internal carotid
(c) anterior cerebral artery
(d) middle cerebral artery Admisson Card A6: Answer Side CORRECT
(d) middle cerebral artery
INCORRECT
(a) basilar artery
(b) internal carotid
(c) anterior cerebral artery
IF CORRECT—CHOOSE PLAYING PIECE AND MOVE ONTO THE BOARD ONE SQUARE ONE AFTER EMERGENCY ROOM. INCORRECT—TRY AGAIN THE TURN AROUND Admission Card A7: Question Side The mechanism which the body uses to deal with ischemic brain tissue is as follows:
(a) necrosis-liquefaction-absorption-scarring
(b) necrosis-callous formation-scarring
(c) necrosis-scerosis-dead callous tissue
(d) leukocytosis-necrosis-scarring Admission Card A7: Answer Side CORRECT
(a) necrosis-liquefaction-absorption and scarring
INCORRECT
(b)
(c)
(d)
CORRECT—CHOOSE A PLAYING PIECE AND MOVE ONTO THE BOARD AND SQUARE ONE AFTER EMERGENCY ROOM. INCORRECT—TRY AGAIN THE NEXT TURN AROUND The following are illustrative examples of representative intervention cards:

Intervention Card 1: Question Side

The client has a motor aphasia. This occurs as result of injury to what area of the brain and involves what deficit specifically?
(a) temporal lobe and means the client cannot read and understand words
(b) Broca's area and means that the client cannot use meaningful language
(c) occupital lobe and means that the client cannot understand the spoken word
(d) parietal lobe and means that the client cannot find the names for things Intervention Card 1: Answer Side

ALL

CORRECT
(b) Broca'e area and means that the client cannot use meaningful language
MOVE FORWARD ONE SQUARE
INCORRECT
(a) (c) (d) Temporal, occipital, parietal Move your client to the transplant room for possible rearrangement of brain tissue. Remain there for one turn. Return to the board on the next turn at the sam square which you left.

Intervention Card 2: Question Side

The client is in a state of stupor. This means:
(a) responds appropriately to all stimuli
(b) response is delayed or incomplete
(c) arounsed by only strong, visual, tactile and auditory stimuli
(d) unresponsive except to very painful stimuli Intervention Card 2: Answer Side

ACUTE*

CORRECT
(c) aroused only by strong visual tactile and auditory stimuli
MOVE FORWARD ONE SQUARE
INCORRECT
(a) (b) (d) responds appropriately, response delayed and unresponsive
Move your client back one square Intervention Card 3: Question Side On admission, the client had a lumbar puncture performed. It was xanthrochromic and the pressure read 220 mm H₂O. This is an indication of:
(a) meningitis
(b) brain tumor
(c) cerebral thrombosis
(d) intracerebral hemorrhage Intervention Card 3: Answer Side

ACUTE*

CORRECT
(d) intracerebral hemorrhage
MOVE FOWARD ONE SQUARE
INCORRECT
(a) meningitis-Move to the lab for study by technicians-then return to the playing field by the nearest red square, next turn.
(b) brain tumor-Move to X-ray for further study and on the next turn, move back to the playing field via the nearest red square
(c) cerebral thrombosis-Move to the OR and then next turn return to the playing field via the nearest red square.

Intervention Card 4: Question Side

In performing a lumbar puncture the doctor wishes to minimize the danger of any neurological damage to the client. For this reason he would insert the needle into the spinal canal at:
(a) level L 1 and 2
(b) level L 3 and 4
(c) level T 11 and T12
(d) level S1 and S2

Intervention Card 4: Answer Side

ACUTE*

CORRECT
(b) Level L 3 and L4

MOVE FORWARD ONE SQUARE
INCORRECT
(a) L 1 and 2-Move to the bowel for retraining-then to rounds and work back to the playing field via the nearest red square, next turn
(c) T 11 and T 12-Move to the physioltherapy department for assessment-then to rounds and work back to the playing field via the nearest red square, next turn
(d) S 1 and S 2-Move to transplant room for study and then move back to playing field via the nearest red square, next turn.

Intervention Card 5: Question Side

In placing the newly admitted stroke client in a unit, the following would be essential:
(a) an overhead trapeze
(b) a bedboard
(c) tracheal suction apparatus
(d) sandbags and a trochanter roll Intervention Card 5: Answer Side

ACUTE* INTERMEDIATE**

CORRECT
(c) tracheal suction apparatus
MOVE FORWARD ONE SQUARE
INCORRECT
(a) (b) (d) Move the client to respiratory therapy for suction and resuscitation and on the next turn return your client back to the playing field via the color square you left (if convalescent-blue)

Intervention Card 6: Question Side

In assessing the client with a stroke, the following would be most indicative of the side of the brain injured.
(a) spasm of the leg or arm on the effected side
(b) edema of the leg or arm on the effected side
(c) the flaccid puffing out of one cheek during respiration
(d) a fixed constricted pupil Intervention Card 6: Answer Side

ACUTE*

CORRECT
(c) the flaccid puffing out of one cheek during respiration.
MOVE FORWARD ONE SQUARE
INCORRECT
(a) (b) (c) spasm, edema, fixed pupil
Stay where you are for one turn if you are on the red area.
If you are in blue or yellow, move back two squares Intervention Card 7: Question Side On the client with a CVA who initially remains comitose when first admitted to the hospital, the following may be a real danger causing permanent damage:
(a) mouth breathing leading to ulcerations
(b) lack of somatic sense, leading to laceration of the tongue from biting it
(c) immobility leading to spastic paralysis
(d) insufficient blink reflex leading to corneal ulcers Intervention Card 7: Answer Side

ACUTE*

CORRECT (d) insufficient blink reflex leading to corneal ulcers
MOVE FORWARD ONE SQUARE
INCORRECT (a)(b)(c) mouth breathing, lack of somatic sense immobility
Stay where you are for one turn if on red
If on blue or yellow, move back to the last square of red before entering the intermediate area.

Intervention Card 8: Question Side

You assess the client's neurological status and find that he has a positive Babinski sign. This is:
  (a) bilateral footdrop with pain on pressure over the long nerves
  (b) dorsiflexion of the great toe with fanning downward of the remaining toes upon lateral and plantar stimulation
  (c) reflex contraction and pain upon extension of a flexed leg.
  (d) severe calf pain upon sharp dorsiflexion of the foot Intervention Card 8: Answer Side

ALL

CORRECT (b) dorsiflexion of the great toe with fanning downward of the remaining toes upon lateral and plantar stimulation.
MOVE FORWARD 2 SQUARES
INCORRECT (a) (c) bilateral footdrop, reflex contraction Move the client to brain damage area. Next turn move the client back to the playing field via whichever color you left (if on yellow, move to blue) through rounds
(d) Move the client to thrombus. Next turn move the client through rounds and back to the playing field via whatever color you left The game proceeds as follows. First, the order of draw is determined in any manner agreeable to the players. Then, in turn, each player draws a card from the admission deck being careful to hold it so that only the question side is visible. The admission deck is covered by a blank card so that, although the player need not necessarily draw the top card, nevertheless, whatever card is drawn, only the question side is visible. The player then makes a choice of answers, and announces the chosen answer to the other players. The card may then be turned over, and if the player's answer is correct, she enters the game by placing her playing piece on the admitting-office area 10. If the player's answer is incorrect, she must await her next turn before drawing again. As her turn to play recurs, she keeps drawing cards from the admission deck until she gives a correct answer, and then her client is admitted to the hospital. Thus, as each person is admitted to the game, she chooses a playing piece, and places it on the playing board 2 at the admitting-office area 10. Preferably the playing pieces are separately identifiable, as by color or letters or numbers. Preferably all the cards in the admission card deck 5 are white.

After all the players have been admitted to the hospital, and their playing pieces are in the admitting-office area 10, the players may then draw from the intervention card deck 6. The sequence of draw from the intervention card deck 6 is according to the sequence in which each player entered the game by placing her playing piece in the admitting-office area 10. In turn, each player draws an intervention card and reads it aloud. The top card of the intervention card deck 6 is blank, so that none of the printed matter on the cards may be seen prior to each draw. Preferably the answer side of each intervention card states whether the correct intervention can be made at any stage, or only at a limited number of stages. This may be done by marking the answer side of the card "ACUTE", "INTERVENTION", "ALL", etc., or by color-coding the answer side. For example, if the acute areas 12 are red, intervention cards having questions relating to the acute stage of a patient's condition may include a red mark on the answer side thereof; if the intermediate areas 13 are blue, intervention cards having questions relating to the intermediate stage of a patient's condition may include a blue mark on the answer side thereof; and if the convalescence areas 14 are yellow, intervention cards having questions relating to the convalescence stage of a patient's condition may include a yellow mark on the answer side thereof. Some questions may properly relate to more than one stage of a patient's condition, and so the answer side of the corresponding card will have more than one colored mark. In this way, a player may sometimes draw an intervention card relating to only one or two of the three stages of a patient's condition. A player may reject any card after reading the question, so that if a player draws an intervention card which does not relate to the same stage as that in which her playing piece is then located, she need not answer the question. But if she does answer the question, even if correctly, a penalty is imposed for not realizing that the question did not pertain to the proper stage. If a reference reader has been designated, the player also tells the reader the number of the card drawn.

All of the questions on the intervention cards relate to a situation regarding the patient or client which requires intervention on the part of the nurse, and the answers set forth various alternative actions, or "interventions", which are available to the nurse. Accordingly, the answers may be referred to as "interventions."

After reading the problem and the possible interventions aloud, the player involved may choose to do any one of the following three things:

(1) She may accept the card and choose one of the listed interventions. After making this choice, the player turns the card over and follows the directions which are pertinent to her chosen answer. The directions will instruct the player to move her playing piece in a certain way, which will be advantageous in the case of a correct answer, and disadvantageous in the case of an incorrect answer. After the playing piece has been moved in accordance with the instructions, time should be allowed to refer to the reference book, in order that all the players may be reminded of the rationale for the correct alternative. This is because the primary purpose of the game is educational, and the reading aloud of the rationale right after the fact situation which gives rise to it has occurred during play, will increase the ability of the players to remember it. The rationale for the correct alternative intervention should always be read aloud. If a reader has been designated, the reader will read aloud the rationale for the correct intervention. In addition, if the player involved made an incorrect choice, and if the player so designates, the reader shall also read aloud the consequences which follow from such incorrect choice: i.e., the medical consequences of the incorrect intervention treatment. If no reader has been designated, the person to the right of the player involved may serve the function of reader for that particular play.

However, during the admission round, in which all the players are drawing cards from the admission card deck 5, the reader only reads the rationale for the answer actually chosen, whether or not it is a correct choice. This is because the cards in the admission card deck 5 may be used more than once during the admission round. During the playing, or intervention, round, even an incorrect answer results in some movement on the playing board; but during the admission round, an incorrect answer results in no progress whatever, and so a multiplicity of incorrect answers can readily use up the entire admission card deck 5 (without, however, revealing any of the correct answers, as long as the reader does not reveal them).

(2) The player may reject the card drawn and choose another. However, this can only be done twice during any game. Since the player does not see the question until the card is drawn, uncertainty as to the correct answer is one reason for rejecting the card drawn. Another reason would be the case in which the player recognizes that the question does not relate to the stage of the patient's condition in which that player's playing piece is located. However, after the second card is chosen and the corresponding play is made, the play continues to the next and subsequent players, and the player who rejected the first card must forfeit her next turn.

(3) The player may hold the first card drawn, and then draw a second card, which is the one played. That is to say, the player answers the question presented on the second card, and plays in accordance with the instructions corresponding to her answer; and then holds on to the first card for future use. However, only three cards can be held for the entire game.

Not only is each player limited to holding on to three cards in any one game, but she must use them before the end of the game, or else incur a penalty. For example, if a player chooses an intervention card that would be applicable in the convalescence stage and her playing piece is in the acute group of areas, she may choose to hold that card until she knows she can use it, but the card must be used before the end of the game, or else a penalty is incurred. The penalties incurred for holding cards when the game is finished are as follows:

If a player wins and is still holding cards with no specific level designation, she must forfeit her win and return to the first area in the convalescence zone on the board, and then play her remaining cards in turn. If a player wins and is still holding cards that have any designation marked intermediate or acute, she must forfeit her win and return to the appropriate level. That is to say, if the cards still held are intermediate level, the player should return her playing piece to the last area in the intermediate zone on the board. If any of the cards still held is acute level, the player must return her playing piece to the last area in the acute zone on the board. In either event, the player then plays her held cards in turn.

In one variant of the game, if an alternative is chosen for an inappropriate level of recovery, a penalty may be imposed. For example, if an alternative is chosen for the acute level that belongs in convalescence, a penalty may be imposed.

In a large group with several quartets/quintets, the following are options:

(1) all the winners of the game to have met the criteria for that class and not be obligated to continue to play. Then require the losers to continue to play until all but the last sequence of games have produced the losers. Then proceed with whatever learning techniques are deemed necessary to correct the losers deficiencies.

(2) Set up the sequence of play like that of military whist and reward the winning players in some way at the end of all game sequences. For example, the winners at the first table (1st and runner up) move to the next table to play the winners at that table while the losers move back and try to win over the losers at the first table and vice versa.

(3) Allow all the readers of the first game sequence to form a quartet and play one another while the winners of the first sequence become the readers.

There are three levels of illness demonstrated on the Board and throughout the game, Acute, Intermediate and Convalescence.

The negative effects of wrongly chosen alternatives are visualized on the board through effected body organs: brain (head), heart, lungs, liver, stomach/esophagus/duodenum, blood vessels, large intestine, muscle, kidneys/ureters/bladder urethra/adrenals and through abnormalities of temperature and blood pressure.

Hospital departments are utilized on the board to emphasize the consequences of wrong alternatives.

The same game board is appropriate for use with any chosen medical pathophysiological condition and the nursing interventions that are relevant to it provided the accompanying materials are in the appropriate form. (Cards and reference texts with listed alternatives and explanations).

A suitable board size is 18"-20" squared, done in four basic colors-red, blue, green, yellow (and black and white).

The game form and components are appropriate for learning/reinforcement, or updating knowledge through review for all levels of nurses from student nurses through graduate nurses in all academic preparations. (Associate Degree, Diploma, Baccalaureate Degree) because the game deals with indepth but basic knowledge of nursing interventions relevant to chosen medical pathophysiological conditions. It also provides information about the conditions themselves. In summary, the content of the game is that pertinent to selective pathophysiological conditions, and the nursing interventions relevant to dealing with them. It is the process, form and methodology of learning information that is original, and exclusive.

It can be seen from the above that the invention herein disclosed has many of the advantages of the type set forth in U.S. Pat. No. 4,121,823, and yet provides a game which is particularly well suited to teaching student nurses and graduate nurses.

Having described the principles of the invention, together with an illustrative embodiment thereof, it is to be understood that, although specific terms are employed, they are used in a generic and descriptive sense, and not for purposes of limitation, the scope of the invention being set forth in the following claims.

I claim:

1. Means for learning, reinforcement, or updating knowledge through review for all levels of nurses from student nurses through graduate nurses in all academic preparations by means of a board game to be used by players who are said nurses comprising in combination a board having (1) a sequential path of spaces the sequence whereof passes through three levels of illness: Acute, Intermediate and Convalescence, (2) visualizations of body organs affected by wrongly chosen alternatives and of abnormalities of temperature and blood pressure and (3) designated areas for hospital departments, including an Admitting Office at the start of said sequence and a Discharge Office at the end of said sequence, each of said levels being indicated by printed matter on said board which designates certain spaces as Acute, certain spaces in Intermediate and certain spaces as Convalescence, the placement of said printed spaces being analogous to and vividly suggestive of the progress of a real patient; a plurality of playing pieces representing clients of said players; a multiplicity of admission playing cards having printed thereon information on certain aspects of a client's illness and alternatives for dealing with them, so that only a correct selection of alternatives will entitle a player to place her playing piece on the board at said Admitting Office, which is located so as vividly to suggest the location of a real admissions office; and a multiplicity of intervention playing cards having printed on one side thereof information on certain other aspects of a client's illness and alternatives for dealing with them, and having printed on the other side thereof (a) consequences of a correct selection of alternatives which direct the player to move playing piece on the board so that it progresses along said sequence toward said Discharge Office, and (b) consequences of an incorrect selection of alternatives which direct the player to impede such progress in a manner correlated to and vividly suggestive of the actual real-life consequence of that particular incorrect alternative, said printed matter on said intervention cards being correlated to the areas on said board and to the actual areas of a real hospital.

* * * * *